[12] United States Patent
Xu et al.

(10) Patent No.: US 11,168,072 B2
(45) Date of Patent: Nov. 9, 2021

(54) CRYSTAL FORM OF MORPHOLINO QUINAZOLINE COMPOUND, PREPARATION METHOD THEREFOR AND USE THEREOF

(71) Applicant: SHANGHAI YINGLI PHARMACEUTICAL CO., LTD, Shanghai (CN)

(72) Inventors: Zusheng Xu, Shanghai (CN); Yangtong Lou, Shanghai (CN)

(73) Assignee: SHANGHAI YINGLI PHARMACEUTICAL CO., LTD, Shanghai (CN)

( * ) Notice: Subject to any disclaimer, the term of this patent is extended or adjusted under 35 U.S.C. 154(b) by 0 days.

(21) Appl. No.: 17/279,185

(22) PCT Filed: Sep. 12, 2019

(86) PCT No.: PCT/CN2019/105688
§ 371 (c)(1),
(2) Date: Mar. 24, 2021

(87) PCT Pub. No.: WO2020/063368
PCT Pub. Date: Apr. 2, 2020

(65) Prior Publication Data
US 2021/0317104 A1    Oct. 14, 2021

(30) Foreign Application Priority Data
Sep. 27, 2018   (CN) .......................... 201811131702.8

(51) Int. Cl.
*C07D 401/14* (2006.01)
(52) U.S. Cl.
CPC ........ *C07D 401/14* (2013.01); *C07B 2200/13* (2013.01)
(58) Field of Classification Search
None
See application file for complete search history.

(56) References Cited

U.S. PATENT DOCUMENTS

| 2009/0318411 A1 | 12/2009 | Castanedo et al. |
| 2010/0298319 A1 | 11/2010 | Nagaraj et al. |
| 2012/0135988 A1 | 5/2012 | Castanedo et al. |
| 2013/0079512 A1 | 3/2013 | Nagaraj et al. |
| 2014/0066620 A1 | 3/2014 | Mysore et al. |
| 2016/0244432 A1 | 8/2016 | Xu et al. |

FOREIGN PATENT DOCUMENTS

| CA | 2926596 A1 | 4/2015 |
| CN | 101889015 A | 11/2010 |
| CN | 102105474 A | 6/2011 |
| CN | 104557872 A | 4/2015 |
| EP | 3059238 A1 | 8/2016 |
| TW | 202024066 A | 7/2020 |
| WO | WO-2009045175 A1 | 4/2009 |
| WO | WO-2009146406 A1 | 12/2009 |
| WO | WO-2015055071 A1 | 4/2015 |

OTHER PUBLICATIONS

International Search Report issued in International Patent Application No. PCT/CN2019/105688, dated Nov. 26, 2019.
International Preliminary Report on Patentability (Chapter I) issued in International Patent Application No. PCT/CN2019/105688, dated Mar. 23, 2021.
Bart et al., "Phosphoinositide 3-kinases: a conserved family of signal transducers", Trends. Biochem. Sci., 1997, 22, pp. 267-272.
Igor et al., "The phosphatidylinositol 3-kinase-AKT pathway in human cancer", Nat. Rev. Cancer, 2002, 2, pp. 489-501.
Pharmacopoeia of the PRC. (2015 version), vol. IV, 0402 Infrared Spectrophotometry.
Written Opinion Of The International Searching Authority for PCT/CN2019/105688, dated Nov. 26, 2019. English translation provided.
Minor Caira Ed—Montchamp Jean-Luc: 11 Crystalline Polymorphism of Organic Compounds 11, TOPI CS in Current Chemistry; [TOPI CS in Current Chemistry], Springer, Berlin, DE, vol. 198, Jan. 1, 1998 (Jan. 1, 1998), pp. 163-208, XP008166276, ISSN: 0340-1022, DOI:10.1007/3-540-69178-2 5 [retrieved on Feb. 26, 1999]* Chapter 3.1 *.

(Continued)

*Primary Examiner* — Heidi Reese
(74) *Attorney, Agent, or Firm* — Harness, Dickey & Pierce, P.L.C.

(57) ABSTRACT

A crystal form I of a morpholino quinazoline compound represented by the following formula A, a preparation method therefor and use thereof. The crystal form I has good stability and non-hygroscopicity, and the preparation method is simple and suitable for industrial production.

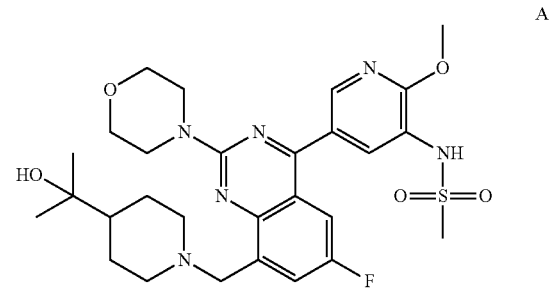

A

10 Claims, 6 Drawing Sheets

(56) References Cited

OTHER PUBLICATIONS

Stephen Byrn et al: "Pharmaceutical Solids: A Strategic Approach to Regulatory Considerations", Pharmaceutical Research, vol. 12, No. 7, Jul. 1, 1995 (Jul. 1, 1995), pp. 945-954, XP055531015, DOI: 10.1023/A:1016241927429 Retrieved from the Internet: URL:https://link.springer.com/article/10.1023/A:1016241927429> * p. 952, right column, line 13ff *.
Extended European Search Report regarding Application No. 19864074.0, dated Aug. 13, 2021.

CRYSTAL FORM OF MORPHOLINO QUINAZOLINE COMPOUND, PREPARATION METHOD THEREFOR AND USE THEREOF

CROSS-REFERENCE TO RELATED APPLICATIONS

This application is a U.S. National Phase Application under 35 U.S.C. 371 of International Application No. PCT/CN2019/105688, filed on Sep. 12, 2019, which claims the priority of Chinese patent application CN201811131702.8 filed on Sep. 27, 2018. The contents of the above applications are incorporated herein by reference in their entireties.

TECHNICAL FIELD

The present disclosure relates to a crystal form of morpholino quinazoline compound, a preparation method and use thereof.

BACKGROUND

A morpholino quinazoline compound with the structure shown in formula A

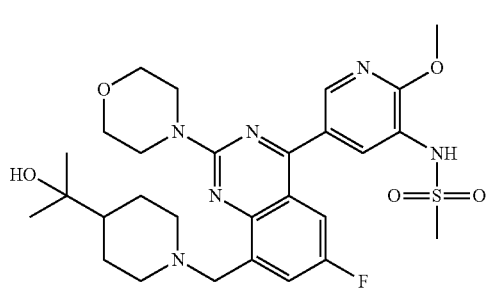

(hereinafter referred to as the morpholino quinazoline compound represented by formula A) has the activity to inhibit phosphatidylinositol 3-kinase δ (PI3K δ).

PI3K δ is an intracellular phosphatidylinositol kinase that catalyzes the 3-position hydroxyl phosphorylation of phosphatidyl alcohols. PI3K can be classified into class I, II and III kinases, and the most widely studied is class I PI3K, which is activated by cell surface receptors. Class I PI3K in mammalian cells is subdivided into classes Ia and Ib based on structure and receptors, which transmit signals from tyrosine kinase-coupled receptors and G protein-coupled receptors, respectively. Class Ia PI3K includes PI3K α, PI3K β, and PI3K δ isoforms, and class Ib PI3K includes PI3K γ isoform (*Trends. Biochem. Sci.*, 1997, 22, 267-272). Class Ia PI3K is a dimeric protein composed of a catalytic subunit p110 and a regulatory subunit p85, with lipid-like kinase and protein kinase dual activities (*Nat. Rev. Cancer.*, 2002, 2, 489-501), and is thought to be associated with cell proliferation and carcinogenesis, immune disorders, and diseases involving inflammation.

WO2015055071A1 discloses the morpholino quinazoline represented by formula A and their preparation methods. The crystal form of the morpholino quinazoline represented by formula A has a critical effect on the stability of the drug during production, processing, storage, and transportation.

The phenomenon that a substance can exist in two or more different crystal structures is called polymorphism. Different solid forms of compounds often exhibit different physical and chemical properties. In the case of drugs, this polymorphism can affect the absorption of the drug and thus the bioavailability of the drug, thereby resulting in different clinical efficacy and toxic side effects. In view of this, it is of great importance to develop crystal forms of the morpholino quinazoline represented by formula A with advantageous properties.

CONTENT OF THE PRESENT INVENTION

The technical problem to be solved by the present invention is to provide a crystal form of the morpholino quinazoline compound represented by formula A, a preparation method thereof and a use thereof. The crystal form is simple to be prepared, suitable for industrial production, and is not easy to absorb moisture, and has good stability, thereby being of great value for the optimization and development of drugs.

The present invention solves the above technical problems by the following technical solutions.

The present disclosure provides a crystal form I of the morpholino quinazoline compound represented by formula A having an X-ray powder diffraction pattern comprising diffraction peaks at angles 2θ of 7.7±0.2°, 9.7±0.2°, 12.4±0.2°, 15.4±0.2°, 17.4±0.2°, 18.0±0.2° and 18.4±0.2°,

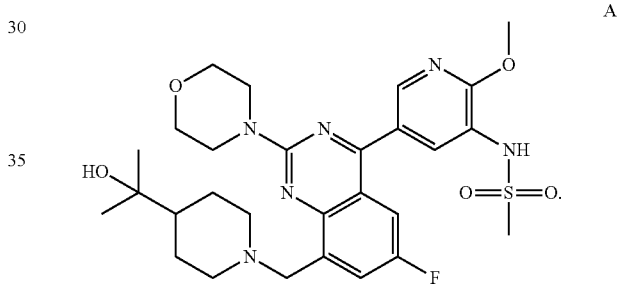

The X-ray powder diffraction pattern of the crystal form I of the morpholino quinazoline compound represented by formula A can further comprise diffraction peaks at one or more of the following angles 2θ: 11.0±0.2°, 11.3±0.2°, 19.5±0.2°, 20.1±0.2°, 21.8±0.2°, 22.6±0.2°, 23.2±0.2°, 23.6±0.2°, 24.3±0.2°, 25.8±0.2°, and 28.7±0.2°.

Preferably, the crystal form I of the morpholino quinazoline compound represented by formula A has an X-ray powder diffraction pattern comprising diffraction peaks at the following angles 2θ: 7.7±0.2°, 9.7±0.2°, 11.0±0.2°, 12.4±0.2°, 15.4±0.2°, 17.4±0.2°, 18.0±0.2°, 18.4±0.2°, 23.6±0.2° and 24.3±0.2°.

More preferably, the crystal form I of the morpholino quinazoline compound represented by formula A has an X-ray powder diffraction pattern comprising diffraction peaks at the following angles 2θ: 7.7±0.2°, 9.7±0.2°, 11.0±0.2°, 11.3±0.2°, 12.4±0.2°, 15.4±0.2°, 17.4±0.2°, 18.0±0.2°, 18.4±0.2°, 19.5±0.2°, 20.1±0.2°, 21.8±0.2°, 22.6±0.2°, 23.2±0.2°, 23.6±0.2°, 24.3±0.2°, 25.8±0.2° and 28.7±0.2°.

In the present disclosure, the crystal form I of the morpholino quinazoline compound represented by formula A can have an X-ray powder diffraction pattern comprising diffraction peaks at the diffraction angles 2θ with peak height percentage shown in Table 1:

TABLE 1

| Number | 2θ (±0.2°) | Percentage of peak height (%) |
|---|---|---|
| 1 | 7.239 | 5.5 |
| 2 | 7.666 | 18.4 |
| 3 | 9.732 | 34.5 |
| 4 | 10.962 | 25.7 |
| 5 | 11.318 | 5.4 |
| 6 | 12.385 | 89.2 |
| 7 | 15.377 | 65.5 |
| 8 | 17.404 | 100.0 |
| 9 | 17.971 | 99.4 |
| 10 | 18.382 | 89.6 |
| 11 | 19.516 | 11.0 |
| 12 | 20.111 | 24.6 |
| 13 | 21.795 | 36.0 |
| 14 | 22.551 | 15.8 |
| 15 | 23.191 | 16.5 |
| 16 | 23.564 | 53.2 |
| 17 | 24.300 | 30.5 |
| 18 | 25.799 | 13.9 |
| 19 | 28.684 | 21.5 |

In the present disclosure, the crystal form I of the morpholino quinazoline compound represented by formula A can also have an X-ray powder diffraction pattern comprising diffraction peaks at the diffraction angles 2θ with peak area percentage shown in Table 2:

TABLE 2

| Number | 2θ (±0.2°) | Percentage of peak height (%) |
|---|---|---|
| 1 | 7.239 | 6.4 |
| 2 | 7.666 | 15.5 |
| 3 | 9.732 | 37.4 |
| 4 | 10.962 | 18.9 |
| 5 | 11.318 | 4.3 |
| 6 | 12.385 | 52.4 |
| 7 | 15.377 | 64.0 |
| 8 | 17.404 | 76.1 |
| 9 | 17.971 | 87.3 |
| 10 | 18.382 | 100.0 |
| 11 | 19.516 | 11.1 |
| 12 | 20.111 | 20.6 |
| 13 | 21.795 | 43.6 |
| 14 | 22.551 | 11.1 |
| 15 | 23.191 | 18.1 |
| 16 | 23.564 | 60.9 |
| 17 | 24.300 | 26.6 |
| 18 | 25.799 | 14.5 |
| 19 | 28.684 | 24.2 |

In the present disclosure, the crystal form I of the morpholino quinazoline compound represented by formula A can also have an X-ray powder diffraction pattern comprising diffraction peaks at the diffraction angles 2θ with peak height percentage and peak area percentage shown in Table 3:

TABLE 3

| Number | 2θ (±0.2°) | d(A) | Percentage of peak height (%) | Percentage of peak area (%) |
|---|---|---|---|---|
| 1 | 7.239 | 12.2016 | 5.5 | 6.4 |
| 2 | 7.666 | 11.5230 | 18.4 | 15.5 |
| 3 | 9.732 | 9.0805 | 34.5 | 37.4 |
| 4 | 10.962 | 8.0645 | 25.7 | 18.9 |
| 5 | 11.318 | 7.8119 | 5.4 | 4.3 |
| 6 | 12.385 | 7.1407 | 89.2 | 52.4 |
| 7 | 15.377 | 5.7574 | 65.5 | 64.0 |
| 8 | 17.404 | 5.0912 | 100.0 | 76.1 |
| 9 | 17.971 | 4.9319 | 99.4 | 87.3 |
| 10 | 18.382 | 4.8225 | 89.6 | 100.0 |
| 11 | 19.516 | 4.5448 | 11.0 | 11.1 |
| 12 | 20.111 | 4.4117 | 24.6 | 20.6 |
| 13 | 21.795 | 4.0743 | 36.0 | 43.6 |
| 14 | 22.551 | 3.9395 | 15.8 | 11.1 |
| 15 | 23.191 | 3.8322 | 16.5 | 18.1 |
| 16 | 23.564 | 3.7724 | 53.2 | 60.9 |
| 17 | 24.300 | 3.6597 | 30.5 | 26.6 |
| 18 | 25.799 | 3.4505 | 13.9 | 14.5 |
| 19 | 28.684 | 3.1096 | 21.5 | 24.2 |

In the present disclosure, the crystal form I of the morpholino quinazoline compound represented by formula A can also have an X-ray powder diffraction pattern expressed by angle 2θ substantially the same as FIG. 1.

In the present disclosure, the X-ray powder diffraction pattern is measured using the Kα ray of Cu target.

In the present disclosure, the crystal form I of the morpholino quinazoline compound represented by formula A can have an infrared absorption spectrum (IR) comprising characteristic peaks at 3445 $cm^{-1}$, 3246 $cm^{-1}$, 3018 $cm^{-1}$, 3001 $cm^{-1}$, 2972 $cm^{-1}$, 2953 $cm^{-1}$, 2924 $cm^{-1}$, 2910 $cm^{-1}$, 2891 $cm^{-1}$, 2850 $cm^{-1}$, 1604 $cm^{-1}$, 1589 $cm^{-1}$, 1552 $cm^{-1}$, 1506 $cm^{-1}$, 1489 $cm^{-1}$, 1458 $cm^{-1}$, 1413 $cm^{-1}$, 1365 $cm^{-1}$, 1155 $cm^{-1}$ and 775 $cm^{-1}$.

In the present disclosure, the crystal form I of the morpholino quinazoline compound represented by formula A can also have an infrared absorption spectrum comprising characteristic peaks, vibrational modes, groups and absorption peak intensity shown in Table 4.

TABLE 4

| Absorption peak wave number ($cm^{-1}$) | Vibrational modes | Group | Absorption peak intensity |
|---|---|---|---|
| 3445 | —O—H stretching vibration | —OH (alcohol) | m (obtuse peak) |
| 3246 | —N—H stretching vibration | —NH (methanesulfonamide) | s |
| 3018, 3001, 2972, 2953, 2924, 2910, 2891, 2850 | —C—H stretching vibration | —CH$_3$, —CH$_2$—, —CH— | m |
| 1604, 1589, 1506, 1489 | Aromatic ring skeleton vibration | Aromatic ring | m |
| 1552 | —NH bending vibration | —NH (methanesulfonamide) | s |
| 1458, 1365 | —C—H bending vibration —OH bending | —CH$_3$, —CH$_2$—, —CH— | s |
| 1413 | vibration (tertiary alcohol) | —OH (alcohol) | s |
| 1365 | —SO$_2$— stretching vibration | —SO$_2$— | s |
| 1155 | —SO$_2$— bending vibration | —SO$_2$— | s |
| 775 | Aromatic ring bending vibration | Aromatic ring | s |

In the present disclosure, the crystal form I of the morpholino quinazoline compound represented by formula A can also have an infrared absorption spectrum substantially the same as shown in FIG. 2.

In the present disclosure, the crystal form I of the morpholino quinazoline compound represented by formula A can also have a thermogravimetric analysis (TGA) graph substantially the same as shown in FIG. 3.

In the present disclosure, the crystal form I of the morpholino quinazoline compound represented by formula A can also have a differential scanning calorimetry (DSC) graph having an absorption peak at 204.3±3° C. and a heat of fusion of 98.70 J/g.

In the present disclosure, the crystal form I of the morpholino quinazoline compound represented by formula A can also have a differential scanning calorimetry graph substantially the same as shown in FIG. 4.

In the present disclosure, the crystal form I of the morpholino quinazoline compound represented by formula A can also have a dynamic vapor sorption (DVS) graph that the crystal form I increases by 0.23% by mass in the relative humidity from 0 to 90% and 0.34% by mass in the relative humidity from 0% to 95% compared to the initial mass.

In the present disclosure, the crystal form I of the morpholino quinazoline compound represented by formula A can also have a dynamic vapor sorption graph substantially the same as shown in FIG. 5.

The present disclosure also provides a method of producing the crystal form I of the morpholino quinazoline compound represented by formula A, which is method 1 or method 2;

method 1: forming the morpholino quinazoline compound represented by formula A in a solvent into a hot saturated solution, and then cooling; the solvent is one or more selected from acetonitrile, 2-methyltetrahydrofuran, acetone, ethyl acetate, ethanol and isopropanol.

The hot saturated solution can be prepared by can referring to conventional preparation methods in the art, preferably, before the cooling step, the hot saturated solution is subject to filtration treatment. The filtration treatment can be performed by conventional filtration methods in the art for such operations, preferably hot filtration. The hot filtration is filter membrane filtration. The pore size of the filter membrane is preferably 0.45 micron.

The cooling can be performed by cooling methods conventionally used for such operations in the art, preferably by rapid cooling method or slow cooling method.

Preferably, when the cooling is performed by rapid cooling method, then the final temperature of the cooling is −15 to −25° C., for example −20° C.

Preferably, when the cooling is performed by slow cooling method, then the cooling is performed at a rate of 5 to 15° C./h, for example 10° C./h.

In the present disclosure, a post-treatment step of filtration and drying can be comprised after the cooling.

The filtration can be performed under conventional conditions and operations for such operations in the art, preferably filtration under reduced pressure. The drying can be performed under conventional conditions and operations for such operations in the art, preferably vacuum drying.

Method 2: mixing the morpholino quinazoline compound represented by formula A in solvent A and solvent B, dissolving and crystallizing;

the solvent A is one or more selected from tetrahydrofuran, 1,4-dioxane, ethanol, ethyl acetate, N,N-dimethylformamide (DMF), N,N-dimethylacetamide (DMAC), and dimethyl sulfoxide (DMSO); the solvent B is one or more selected from n-heptane, n-hexane, cyclohexane, cyclopentane, n-pentane, petroleum ether, and water.

Preferably, when the solvent A is one or more selected from tetrahydrofuran, 1,4-dioxane, ethanol and ethyl acetate, then the solvent B is one or more selected from n-heptane, n-hexane, cyclohexane, cyclopentane, n-pentane and petroleum ether.

Preferably, when the solvent A is one or more selected from N,N-dimethylformamide (DMF), N,N-dimethylacetamide (DMAC) and dimethyl sulfoxide (DMSO), then the solvent B is water.

The crystallizing can be performed by conventional methods for such operations in the art. Preferably, the crystallizing can be performed by natural cooling to room temperature.

The condition for dissolving can be conventional conditions in the art for such operations. Preferably, the condition for dissolving is heating; more preferably, heating accompanied with stirring.

The heating is generally performed at a temperature of the boiling point of the solvent in which the morpholino quinazoline compound represented by formula A is dissolved, preferably 40 to 90° C., for example 50° C.

The stirring can be performed at a speed of 200 to 350 rpm, for example 260 rpm.

Preferably, a filtration step can be comprised after the dissolving. The filtration can be performed by conventional methods for such operations in the art, preferably filter membrane filtration. The pore size of the filter membrane is preferably 0.45 micron.

The method 2 is further preferably: dissolving the morpholino quinazoline compound represented by formula A in the solvent A to obtain a mixed solution, adding the solvent B to the mixed solution and crystallizing.

Preferably, the adding can be dropwise adding.

In the present disclosure, a post-treatment step of filtration and drying can be comprised after the crystallizing.

The filtration can be performed under conventional conditions and operations conventional for such operations in the art, preferably filtration under reduced pressure. The drying can be performed under conventional conditions and operations for such operations in the art, preferably vacuum drying.

The present disclosure also provides a use of the crystal form I of the morpholino quinazoline compound represented by formula A in the preparation of a PI3 kinase inhibitor.

Wherein, the PI3 kinase inhibitor can be an in vivo or in vitro kinase inhibitor.

Wherein, the kinase is preferably the p110 S isoform of PI3 kinase (PI3K).

The present disclosure also provides a use of the crystal form I of the morpholino quinazoline compound represented by formula A in the preparation of a medicament for the prevention and/or treatment of a disease associated with PI3 kinase.

In the present disclosure, the kinase is preferably the p110 S isoform of PI3 kinase (PI3K).

In the present disclosure, the disease associated with PI3 kinase includes, but is not limited to, one or more of cancer, immune diseases, metabolic and/or endocrine disorders, cardiovascular diseases, viral infections and inflammation, and neurological diseases, preferably cancer and/or immune diseases.

Wherein, the immune diseases include, but are not limited to, one or more of rheumatoid arthritis, psoriasis, ulcerative colitis, Crohn's disease, and systemic lupus erythematosus; the cardiovascular diseases include, but are not limited to, hematologic neoplasms; and the viral infections and inflammation include, but are not limited to, asthma and/or atopic dermatitis.

The present disclosure also provides a use of the crystal form I of the morpholino quinazoline compound represented by formula A in the preparation of a medicament for the prevention and/or treatment of a disease, the disease being one or more of cancer, immune diseases, metabolic and/or endocrine disorders, cardiovascular diseases, viral infections, inflammation, and neurological diseases.

Wherein, the immune diseases, the cardiovascular diseases, the viral infections and inflammation are as described above.

The present disclosure also provides a use of the crystal form I of the morpholino quinazoline compound represented by formula A in the preparation of a medicament, the medicament being used in combination with another therapeutic agent for the prevention and/or treatment of a disease associated with PI3 kinase.

Wherein, the disease associated with PI3 kinase is as described above.

Wherein, the another therapeutic agent can be used for the prevention and/or treatment of a disease associated with PI3 kinase. The disease can be one or more of cancer, immune diseases (e.g., rheumatoid arthritis, psoriasis, ulcerative colitis, Crohn's disease, and systemic lupus erythematosus), metabolic and/or endocrine disorders, cardiovascular diseases (e.g., hematologic tumors), viral infections, inflammation (e.g., asthma and/or atopic dermatitis), and neurological diseases.

The present disclosure also provides a pharmaceutical composition comprising the crystal form I of the morpholino quinazoline compound represented by formula A, and a pharmaceutically acceptable carrier.

The present disclosure also provides a use of the pharmaceutical composition in the preparation of a medicament for the prevention and/or treatment of a disease associated with PI3 kinase.

Wherein, the disease associated with PI3 kinase is as above described.

In the present disclosure, the crystal form I of the morpholino quinazoline compound represented by formula A can also be used in combination with one or more other active ingredients; when used in combination, the active ingredients can be separate compositions for simultaneous administration or separate administration at different time points in therapy by the same or different routes of administration, or they can be administered together in the same pharmaceutical composition.

In the present disclosure, there are no special restrictions on the method of administration of the pharmaceutical composition, which can be administered in a variety of dosage forms depending on the patient's age, gender and other conditions and symptoms; for example, tablets, pills, solutions, suspensions, emulsions, granules or capsules for oral administration; injections can be administered alone or mixed with delivery solutions for injection (e.g., glucose solutions and amino acid solutions) for intravenous administration; suppositories can be delivered into the rectum.

In some embodiments, the crystal form I of the morpholino quinazoline compound represented by formula A does not undergo transformation when made into a formulation with one or more pharmaceutically acceptable carriers and/or excipients and/or diluents.

In other embodiments, the crystal form I of the morpholino quinazoline compound represented by formula A can be dissolved when made into a pharmaceutical composition. The present disclosure also provides a method of treating a disease comprising administering, to a subject in need of the treatment a therapeutically effective amount of the crystal form I of the morpholino quinazoline compound represented by formula A or the pharmaceutical composition; the disease being a disease associated with PI3 kinase.

Wherein, the disease is preferably one or more of cancer, immune diseases, metabolic and/or endocrine disorders, cardiovascular diseases, viral infections, inflammation, and neurological diseases.

In one embodiment of the present disclosure, the subject is a person suffering from a disease associated with PI3 kinase as described above.

In the present disclosure, "prevention" refers to "prophylaxis". "Prophylaxis" means a reduction in the risk of acquiring or developing a disease or disorder (i.e., at least one of the clinical symptoms of the disease not occurring in a subject who may have been exposed to an agent causing the disease or in a subject susceptible to the disease prior to its onset).

In the present disclosure, "treatment" means improving a disease or disorder (i.e., stopping the disease or reducing its manifestations, the degree or severity of its clinical symptoms); or, improving at least one physical parameter that cannot be perceived by the subject; or slowing disease progression.

The crystal form of the present disclosure can be identified by one or several solid-state analytical methods. For example, X-ray powder diffraction, single crystal X-ray diffraction, infrared absorption spectroscopy, differential scanning calorimetry, thermogravimetric curves, etc. The person skilled in the art knows that the peak intensity and/or peak profile can vary depending on the experimental conditions in X-ray powder diffraction. Also, the measured 2θ values will have an error of about ±0.2° due to the different accuracy of the instruments. And the relative intensity values of the peaks depend more on certain properties of the measured sample than the position of the peaks, such as the size and purity of the crystal form, so the measured peak intensity can show a deviation of about ±20%. Despite experimental errors, instrumental errors and orientation preferences, etc., a person skilled in the art can obtain sufficient information to identify individual crystal form from the X-ray powder diffraction data provided in this patent. In IR spectroscopy measurement, the shape of the spectrum and the position of the absorption peaks are affected to some extent due to the different performance of various types of instruments, differences in the degree of grinding during preparation of the test article, or different degrees of water absorption. In the DSC measurement, the initial temperature, maximum temperature of the absorption peaks and heat of fusion data obtained from the actual measurement have some degree of variability depending on the heating rate, crystal shape and purity and other measurement parameters.

In the present disclosure, the term "rapid cooling" refers to a process of cooling a saturated hot solution by placing it directly at a temperature well below the boiling point of the solvent in the saturated solution (e.g., −20° C.), which has quick cooling rate.

In the present disclosure, the term "slow cooling" refers to a process cooling a hot saturated solution to room temperature at a rate of 5 to 15° C./h (e.g., 10° C./h), which has slow cooling rate.

In the present disclosure, "room temperature" means "10-30° C.".

Each of the above preferred conditions can be arbitrarily combined to obtain a preferred example of the invention without violating the common knowledge in the art.

The reagents and raw materials used in this invention are commercially available.

The positive progressive effect of the present disclosure is that the crystal form I of the morpholino quinazoline compound represented by formula A is simple to be prepared, has good stability and is not easily hygroscopic, thereby being of great value for the optimization and development of drugs.

DETAILED DESCRIPTION OF THE EMBODIMENT

The present invention is further described below by way of embodiments, but the invention is not thereby limited to the described embodiments. Experimental methods for which specific conditions are not indicated in the following embodiments are selected according to conventional methods and conditions, or according to the products' description.

Testing Method

| Instrument | | |
|---|---|---|
| Instrument | Model | Manufacturer |
| Powder X-ray diffractometer | D8 ADVANCE | BRUKER |
| Fourier transform infrared spectroscopy | Presitage 21 | Shimadzu |
| Differential Scanning Calorimeter | Q1000 | TA |
| Thermogravimetric analyzer | Q500 | TA |
| Dynamic vapor sorption analysis | Advantage | SMS |

Powder X-ray diffraction analysis (XRPD): the light source is CuK, the X-ray intensity is 40 KV/40 mA, the scanning mode is Theta-theta, the scanning angle range is 4°-40°, the step size is 0.05°, and the scanning speed is 0.5 sec/step.

Infrared absorption spectroscopy (IR): according to the IR spectrophotometric method in fourth general rule 0402 of Chinese Pharmacopoeia 2015 edition, the test article was prepared by the potassium bromide tablet press method, and the IR absorption spectra were collected in the wave number range of 4000-400 $cm^{-1}$. The number of scans for the test article was 45, and the resolution of the instrument was 4 $cm^{-1}$.

Differential scanning calorimetry (DSC): 2-4 mg of the sample was weighed and placed in an unsealed aluminum tray in a nitrogen flow (50 mL/min) environment, the sample was equilibrated at 25° C., and then heated from 25° C. to 300° C. or 400° C. at a heating rate of 10° C./min.

Thermal gravimetric analysis (TGA): 8-12 mg of the sample was weighed and placed in a platinum sample tray in a nitrogen flow (50 mL/min) environment and heated from 25° C. to 300° C. or 400° C. at a heating rate of 10° C./min.

Dynamic vapor sorption analysis (DVS): about 10 mg of the sample was taken and dried for 60 minutes under a temperature set at 25° C. and a humidity of 0% RH, and then the moisture sorption characteristics of the sample when the humidity changed from 0% RH to 95% RH was tested, and the moisture desorption characteristics of the sample when the humidity changed from 95% RH to 0% RH was tested; the humidity change step was 5% RH; the value of the mass change rate dm/dt less than 0.002% was considered as balance equilibrium, the rate of mass change within 5 minutes less than 0.01%/minute was considered as the equilibrium standard in the testing process, and the maximum equilibrium time was 2 hours. The isothermal water adsorption/desorption characteristics under this test condition were determined and XRPD detection was performed on the samples after the DVS test.

Figure 10:
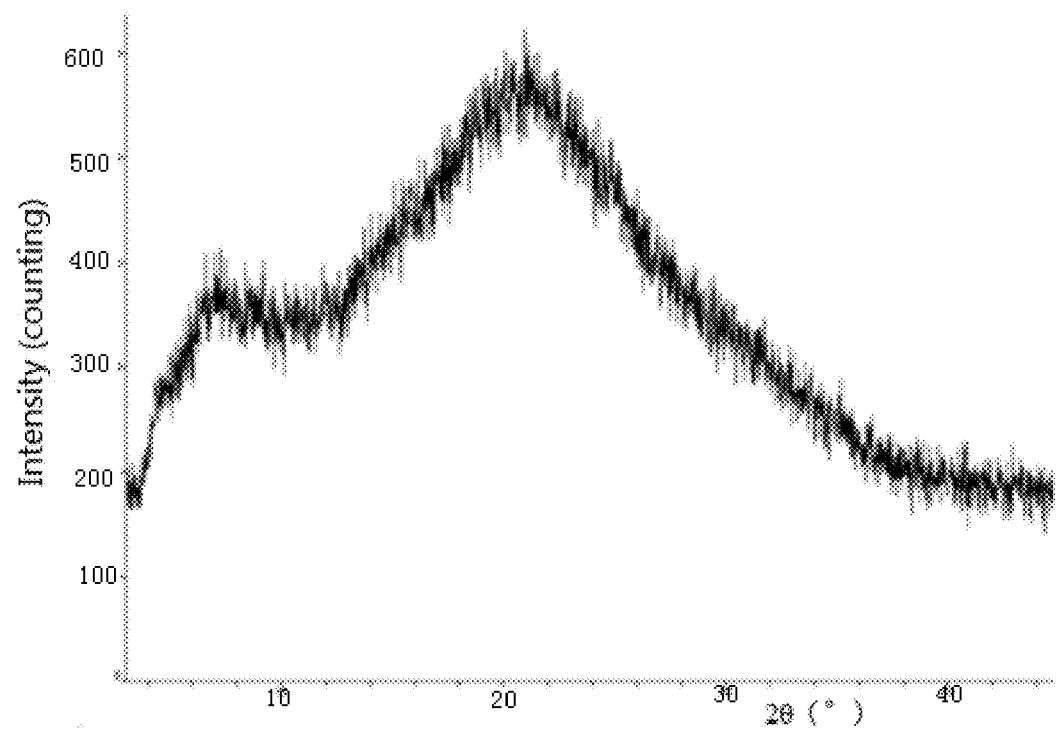
FIG. 10 is the X-ray powder diffraction pattern of the morpholino quinazoline compound represented by formula A in amorphous form obtained by the method of patent WO2015055071A1.

The morpholino quinazoline compound represented by formula A was prepared according to the synthesis method of Example 10 in patent WO2015055071A1 and was characterized as amorphous by XRPD, and its XRPD pattern is shown in FIG. 10.

Example 1: Preparation of the Crystal Form I of the Morpholino Quinazoline Compound Represented by Formula A About 20 mg of the morpholino quinazoline compound represented by formula A was weighed and placed into a vial, a certain volume of acetonitrile was added into the vial, sonicated for 2 min, and then the sample vial was placed on a magnetic heating stirrer with temperature controlled at 50° C. and speed at 260 rpm to promote the dissolution of the sample by heating; if the solution had become clarified, a certain amount of solid sample was added, and the heating was continued to promote dissolution to ensure that finally a supersaturated solution of the sample was obtained, then the supersaturated solution was filtered with a 0.45 micron filter membrane while hot and transferred into a new vial. The vial was immediately placed in a −20° C. refrigerator, the precipitated solid was filtered to obtain the sample.

Figure 1:
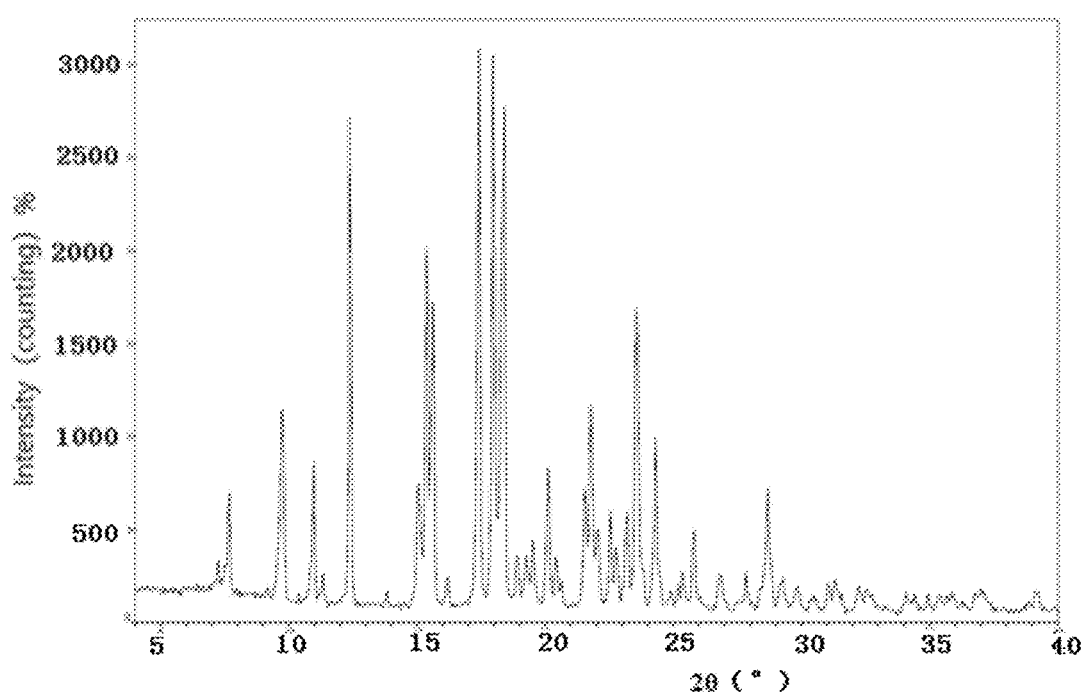
FIG. 1 is the X-ray powder diffraction pattern of the crystal form I of the morpholino quinazoline compound represented by formula A obtained in Example 1.

The sample obtained was determined to be crystal form I by X-ray powder diffraction. The X-ray powder diffraction pattern is shown in FIG. 1, having diffraction peaks at angles 2θ of 7.7±0.2°, 9.7±0.2°, 11.0±0.2°, 11.3±0.2°, 12.4±0.2°, 15.4±0.2°, 17.4±0.2°, 18.0±0.2°, 18.0±0.2° 0.2°, 18.4±0.2°, 19.5±0.2°, 20.1±0.2°, 21.8±0.2°, 22.6±0.2°, 23.2±0.2°, 23.6±0.2°, 24.3±0.2°, 25.8±0.2° and 28.7±0.2°.

Figure 2:
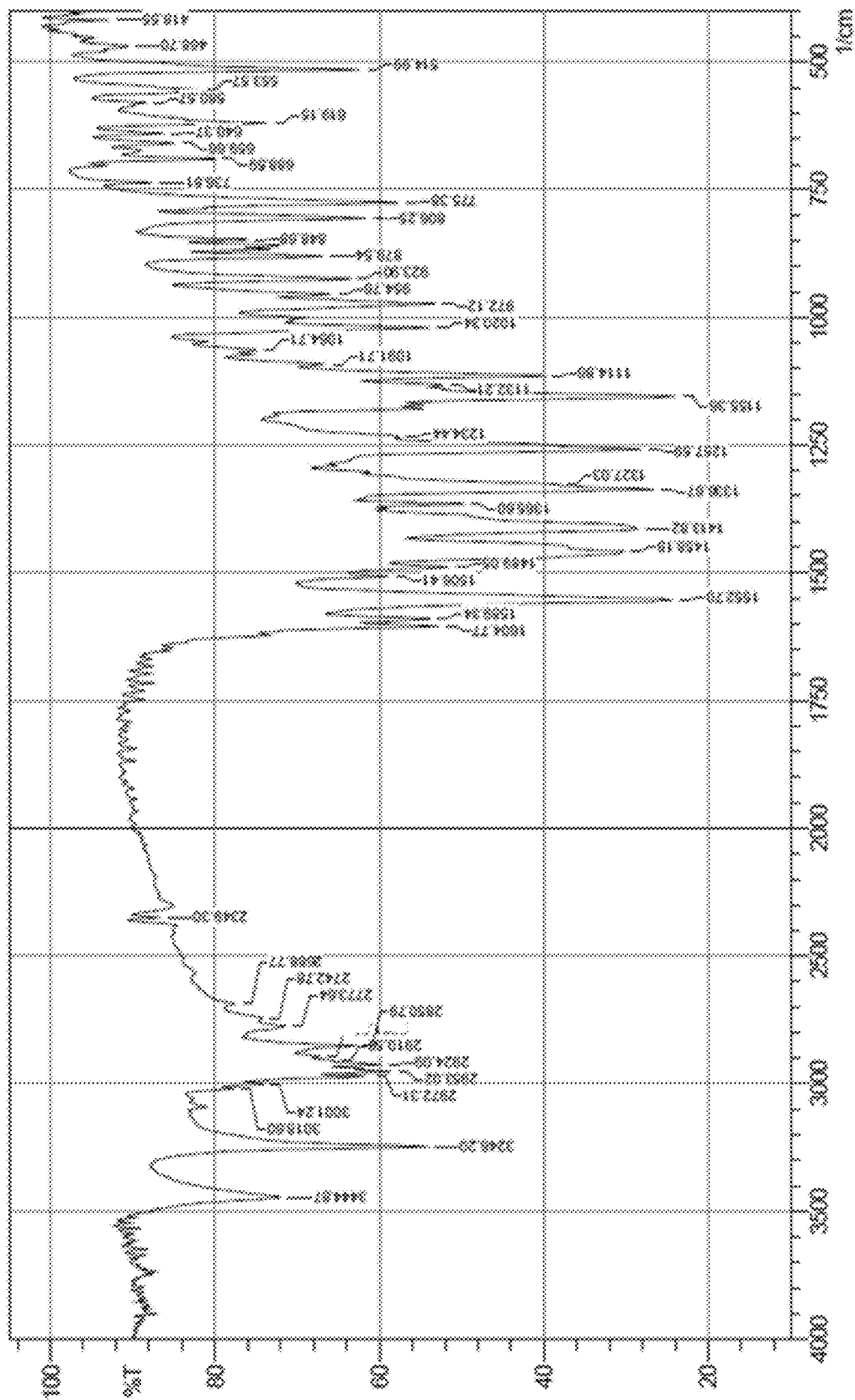
FIG. 2 is the infrared absorption spectrum of the crystal form I of the morpholino quinazoline compound represented by formula A obtained in Example 1.

Its IR spectrum is shown in FIG. 2, with characteristic peaks at 3445 $cm^{-1}$, 3246 $cm^{-1}$, 3018 $cm^{-1}$, 3001 $cm^{-1}$, 2972 $cm^{-1}$, 2953 $cm^{-1}$, 2924 $cm^{-1}$, 2910 $cm^{-1}$, 2891 $cm^{-1}$, 2850 $cm^{-1}$, 1604 $cm^{-1}$, 1589 $cm^{-1}$, 1552 $cm^{-1}$, 1506 $cm^{-1}$, 1489 $cm^{-1}$, 1458 $cm^{-1}$, 1413 $cm^{-1}$, 1365 $cm^{-1}$, 1155 $cm^{-1}$, 775 $cm^{-1}$.

Figure 3:
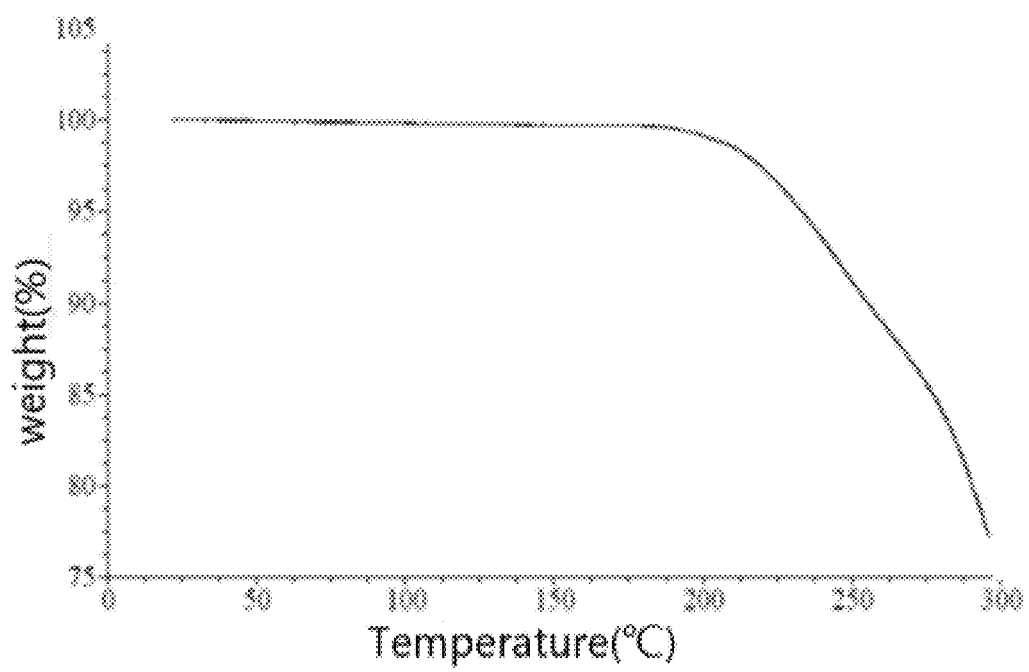
FIG. 3 is the thermogravimetric analysis graph of the crystal form I of the morpholino quinazoline compound represented by formula A obtained in Example 1.

The TGA graph is shown in FIG. 3. From FIG. 3, it can be seen that the crystal form I is anhydrous and contains no water or solvent.

Figure 4:
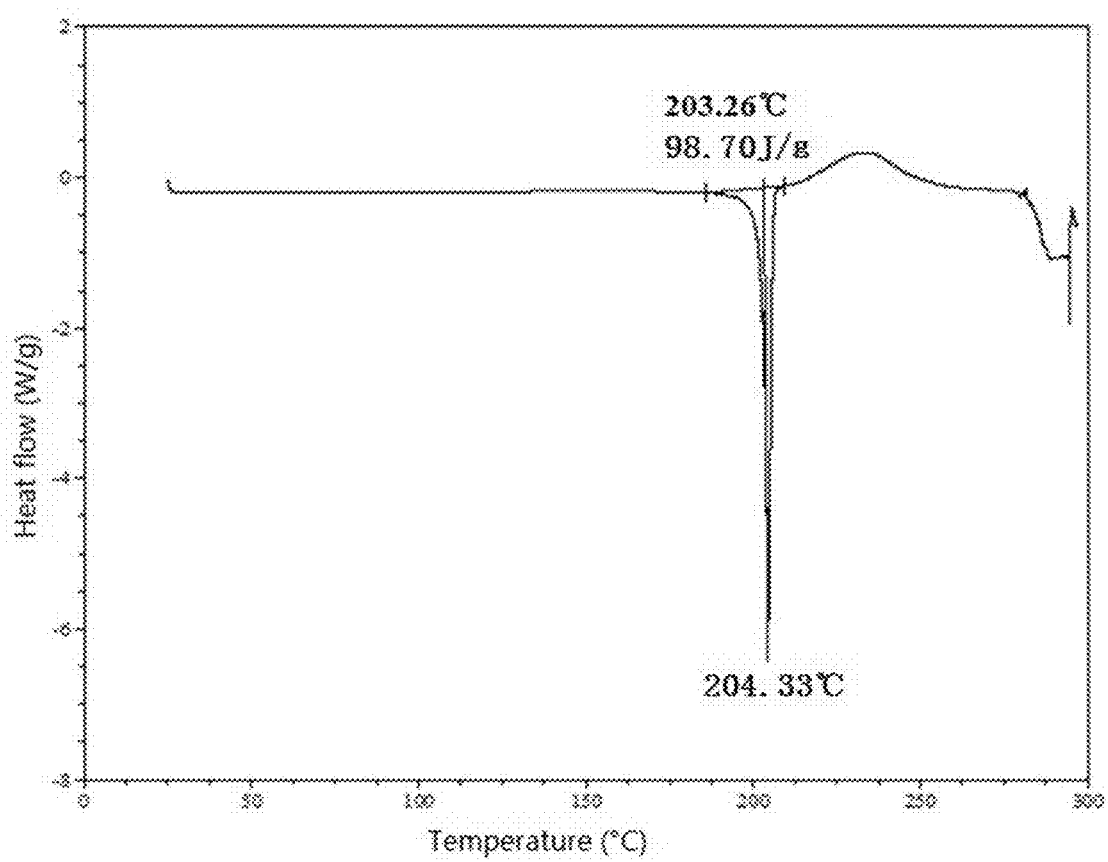
FIG. 4 is the differential scanning calorimetry graph of the crystal form I of the morpholino quinazoline compound represented by formula A obtained in Example 1.

The DSC graph is shown in FIG. 4. The differential scanning calorimetry of the crystal form I has an absorption peak at 204.3±3° C. and a heat of fusion of 98.70 J/g.

Figure 5:
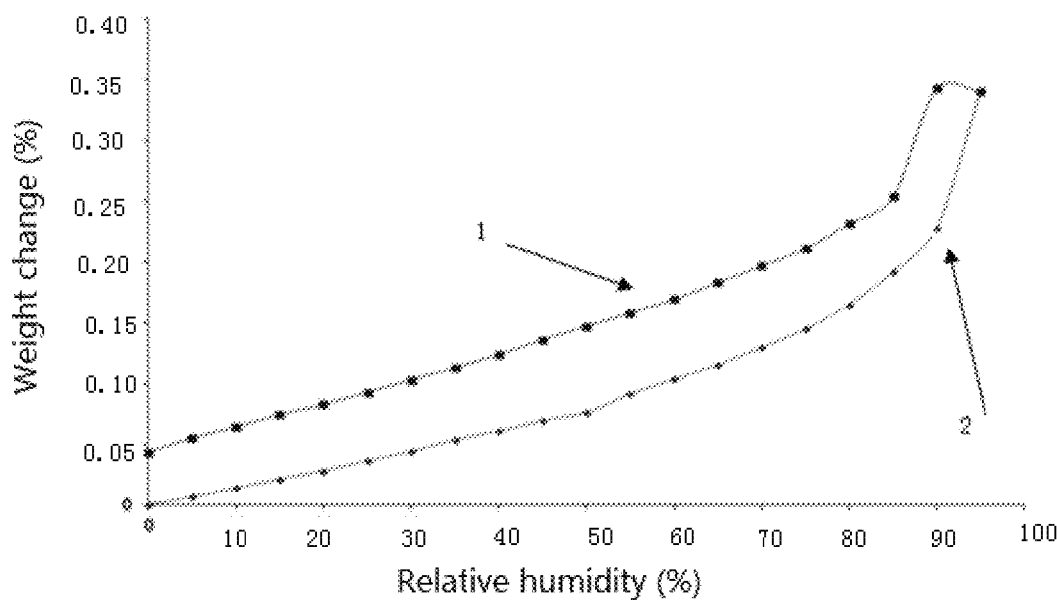
FIG. 5 is the dynamic vapor sorption graph of the crystal form I of the morpholino quinazoline compound represented by formula A obtained in Example 1; where 1 is the moisture desorption curve and 2 is the moisture absorption curve.

The DVS graph is shown in FIG. 5. The dynamic vapor sorption graph of the crystal form I shows that the crystal form I increases by 0.23% by mass in the relative humidity from 0 to 90% and 0.34% by mass in the relative humidity from 0% to 95% compared to the initial mass.

Example 2: Preparation of the Crystal Form I of the Morpholino Quinazoline Compound Represented by Formula A About 20 mg of the morpholino quinazoline compound represented by formula A was weighed and placed into a vial, a certain volume of acetonitrile was added into the vial, sonicated for 2 min, and then the sample vial was placed on a magnetic heating stirrer with temperature controlled at 50° C. and speed at 260 rpm to promote the dissolution of the sample by heating; if the solution had become clarified, a certain amount of solid sample was added, and the heating was continued to promote dissolution to ensure that finally a supersaturated solution of the sample was obtained, then the supersaturated solution was filtered with a 0.45 micron filter membrane while hot and transferred into a new vial. The solution was slowly cooled to room temperature (25° C.) at a rate of 10° C./h and stirred overnight at room temperature, then the precipitated solid was filtered to obtain the sample. The X-ray powder diffraction pattern of the sample obtained by this method was compared with the pattern of Example 1 and determined to be crystal form I.

Example 3: Preparation of the Crystal Form I of the Morpholino Quinazoline Compound Represented by Formula A The method was the same as Example 2 except that the solvent was changed to 2-methyltetrahydrofuran, acetone, ethyl acetate, ethanol and isopropanol, the precipitated solid was filtered to obtain the sample. The X-ray powder diffraction pattern of the sample obtained by this method was compared with the pattern of Example 1 and determined to be crystal form I.

Example 4: Preparation of the Crystal Form I of the Morpholino Quinazoline Compound Represented by Formula A About 1 g of the morpholino quinazoline compound represented by formula A, followed by adding 5 mL of acetone and heating to dissolve, then stopping the heating and allowing it to stand overnight. The next day, filtering and drying to obtain the sample. The X-ray powder diffraction pattern of the sample obtained by this method was compared with the pattern of Example 1 and determined to be crystal form I.

Example 5: Preparation of the Crystal Form I of the Morpholino Quinazoline Compound Represented by Formula A About 20 mg of the morpholino quinazoline compound represented by formula A was weighed and placed into a vial, a certain volume of tetrahydrofuran was added into the vial, sonicated for 2 min, and then the sample vial was placed on a magnetic heating stirrer with temperature controlled at 50° C. and speed at 260 rpm to promote the dissolution of the sample by heating; if the solution had become clarified, a certain amount of solid sample was added, and the heating was continued to promote dissolution to ensure that finally a supersaturated solution of the sample was obtained, then the supersaturated solution was filtered with a 0.45 micron filter membrane while hot and transferred into a new vial; to the new vial was slowly dropwise added n-heptane in a volume by 10 times while keeping slowly stirring, then the precipitated solid was filtered to obtain the sample. The X-ray powder diffraction pattern of the sample obtained by this method was compared with the pattern of Example 1 and determined to be crystal form I.

Example 6: Preparation of the Crystal Form I of the Morpholino Quinazoline Compound Represented by Formula A The method was the same as Example 5 except that the solvent tetrahydrofuran was replaced by dioxane, the antisolvent was n-heptane, which was dropwise added in a volume by 13 times. The X-ray powder diffraction pattern of the sample obtained by this method was compared with the pattern of Example 1 and determined to be crystal form I.

Example 7: Preparation of the Crystal Form I of the Morpholino Quinazoline Compound Represented by Formula A At room temperature, 1 g of the morpholino quinazoline compound represented by formula A was dissolved in 5.5 mL of DMF, 1 mL of water was slowly added with stirring, and the precipitated solid was filtered to obtain the sample. The X-ray powder diffraction pattern of the sample obtained by this method was compared with the pattern of Example 1 and determined to be crystal form I.

Example 8: Preparation of the Crystal Form I of the Morpholino Quinazoline Compound Represented by Formula A 500 mL of ethanol added to 10 g of the morpholino quinazoline compound represented by formula A, which was dissolved completely under heating, then filtered while hot; the filtrate was concentrated to 50-70 mL, and then stirred overnight at room temperature, n-heptane was added until a large amount of solids were precipitated; the precipitated solid was filtered, and dried under vacuum at less than 85° C. for 5-6 hours to obtain the sample. The X-ray powder diffraction pattern of the sample obtained by this method was compared with the pattern of Example 1 and determined to be crystal form I.

Example 9: Preparation of the Crystal Form I of the Morpholino Quinazoline Compound Represented by Formula A 25 mL of ethanol and 25 mL of n-heptane were added to 5 g of the morpholino quinazoline compound represented by formula A, refluxed for 16 hours, cooled to room temperature, filtered, and dried under vacuum at less than 85° C. for 16 hours to obtain about 4 g of the sample. The X-ray powder diffraction pattern of the sample obtained by this method was compared with the pattern of Example 1 and determined to be crystal form I.

Example 10: Preparation of the Crystal Form I of the Morpholino Quinazoline Compound Represented by Formula A At room temperature, 5.5 mL of DMSO was added to 5 g of the morpholino quinazoline compound represented by formula A, 5 mL of water was slowly added and a solid was precipitated, the solid was filtered, and dried under vacuum at less than 85° C. for 17 hours to obtain the sample. The X-ray powder diffraction pattern of the sample obtained by this method was compared with the pattern of Example 1 and determined to be crystal form I.

Example 11 Preparation of the Crystal Form I of the Morpholino Quinazoline Compound Represented by Formula A At room temperature, 360 g of ethyl acetate was added to 6 g of the morpholino quinazoline compound represented by formula A, and then concentrated to half volume; about 60 g of n-heptane was added, and a solid was precipitated; the solid was filtered and dried under vacuum at less than 85° C. for 48 hours to obtain the sample. The X-ray powder diffraction pattern of the sample obtained by this method was compared with the pattern of Example 1 and determined to be crystal form I.

Comparative Example 1: Preparation of the Crystal Form II of the Morpholino Quinazoline Compound Represented by Formula A 30 mg of the morpholino quinazoline compound represented by formula A was weighed and placed into a vial, and 1,4-dioxane/isopropyl ether (v/v=1:1) was added to the vial; the sample was sonicated to promote dissolution; if the solution had become clarified, a certain amount of solid sample was added, and sonicated to promote dissolution to ensure that finally a supersaturated solution of the sample was obtained, then the supersaturated solution was filtered with a 0.45 micron filter membrane and transferred into a new vial; the new vial was left open and the solvent was evaporated naturally at room temperature, the solid obtained was the crystal form II of the morpholino quinazoline compound of represented by formula A.

Figure 6:
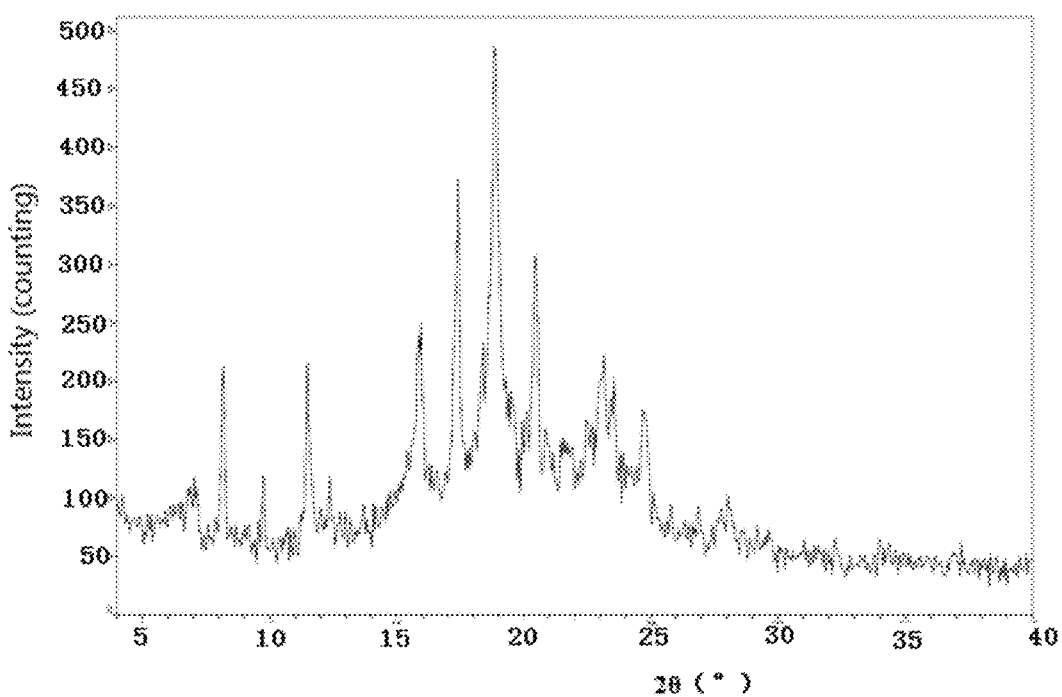
FIG. 6 is the X-ray powder diffraction pattern of the crystal form II of the morpholino quinazoline compound represented by formula A obtained by Comparative Example 1.

The X-ray powder diffraction pattern of the crystal type II of the morpholino quinazoline compound represented by formula A is shown in FIG. 6, wherein 2θ, d(A), peak height and peak area are shown in Table 5 below.

TABLE 5

| 2θ(°) | d(A) | Peak height (Height) | Percentage of peak height (I %) | Peak area (Area) | Percentage of peak area (I %) |
| --- | --- | --- | --- | --- | --- |
| 8.179 | 10.8013 | 148 | 41.8 | 570 | 16.0 |
| 9.758 | 9.0563 | 58 | 16.4 | 120 | 3.4 |
| 11.500 | 7.6882 | 141 | 39.8 | 446 | 12.5 |
| 15.952 | 5.5512 | 143 | 40.4 | 1098 | 30.8 |
| 17.402 | 5.0917 | 243 | 68.6 | 1042 | 29.2 |
| 18.861 | 4.7012 | 354 | 100.0 | 3564 | 100.0 |
| 20.461 | 4.3369 | 180 | 50.8 | 1060 | 29.7 |
| 23.141 | 3.8404 | 105 | 29.7 | 1339 | 37.6 |
| 24.707 | 3.6004 | 79 | 22.3 | 621 | 17.4 |
| 26.866 | 3.3158 | 27 | 7.6 | 81 | 2.3 |

Figure 7:
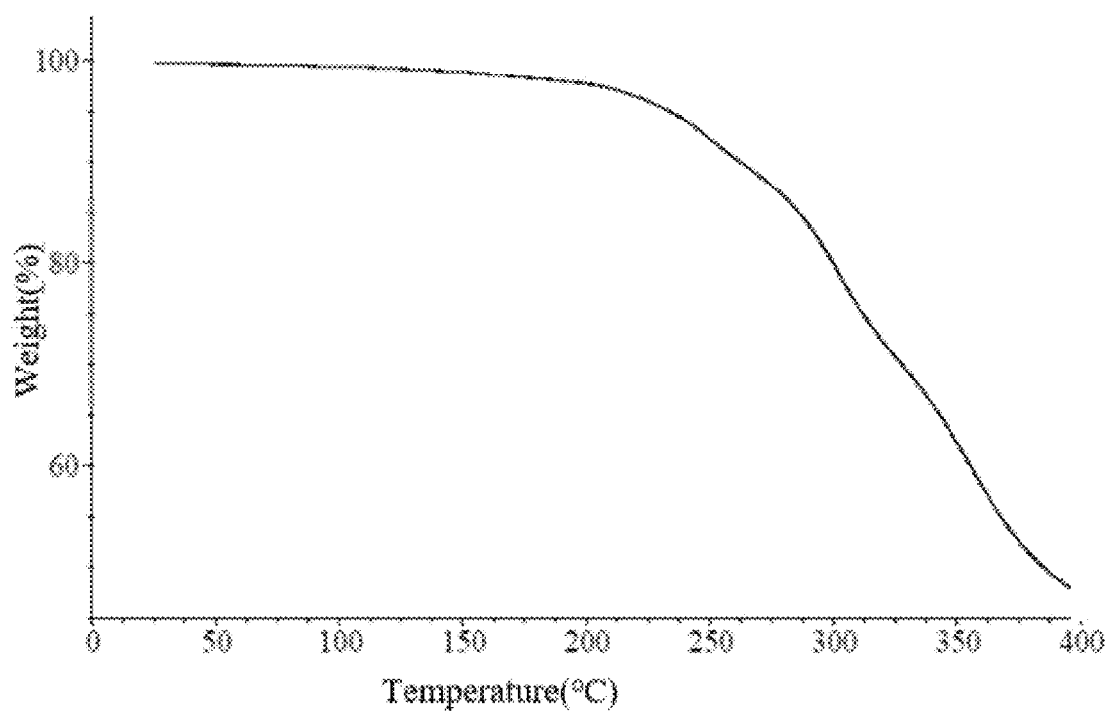
FIG. 7 is the thermogravimetric analysis graph of the crystal form II of the morpholino quinazoline compound represented by formula A obtained by Comparative Example 1.

The TGA graph is shown in FIG. 7. From FIG. 7, it can be seen that the crystal form II of the morpholino quinazoline compound represented by formula A is anhydrous.

Figure 8:
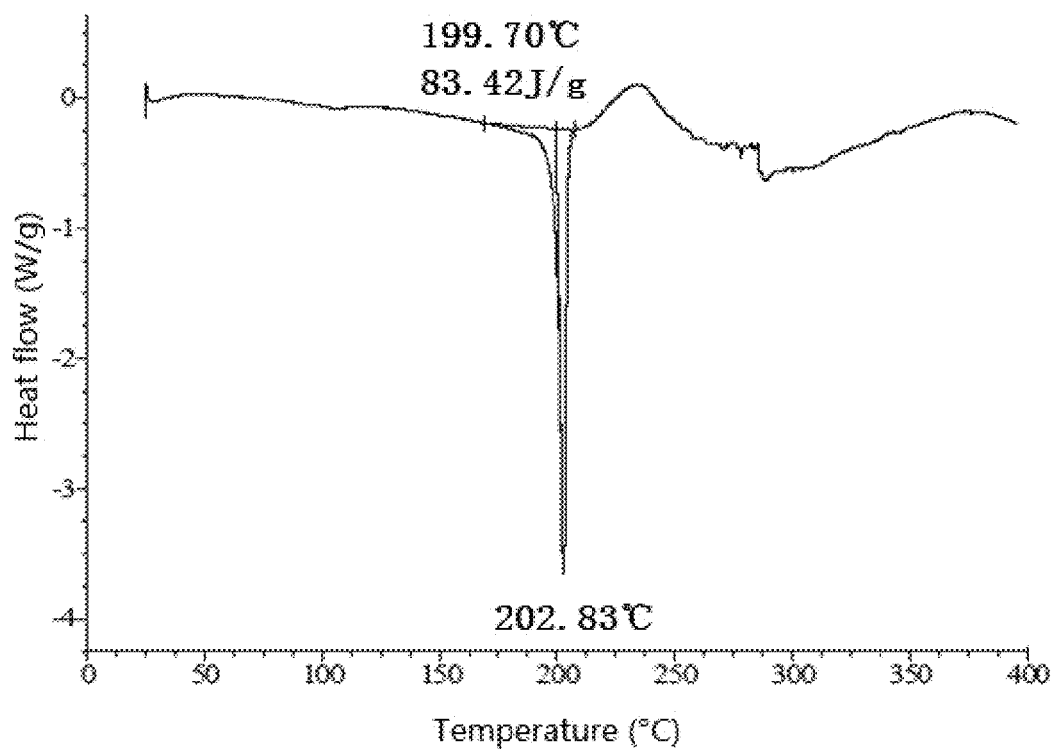
FIG. 8 is the differential scanning calorimetry graph of the crystal form II of the morpholino quinazoline compound represented by formula A obtained by Comparative Example 1.

The DSC graph is shown in FIG. 8. The crystal type II of the morpholino quinazoline compound represented by formula A have an absorption peak at 202.83±3° C. and a heat of fusion of 83.42 J/g in differential scanning calorimetry.

Figure 9:
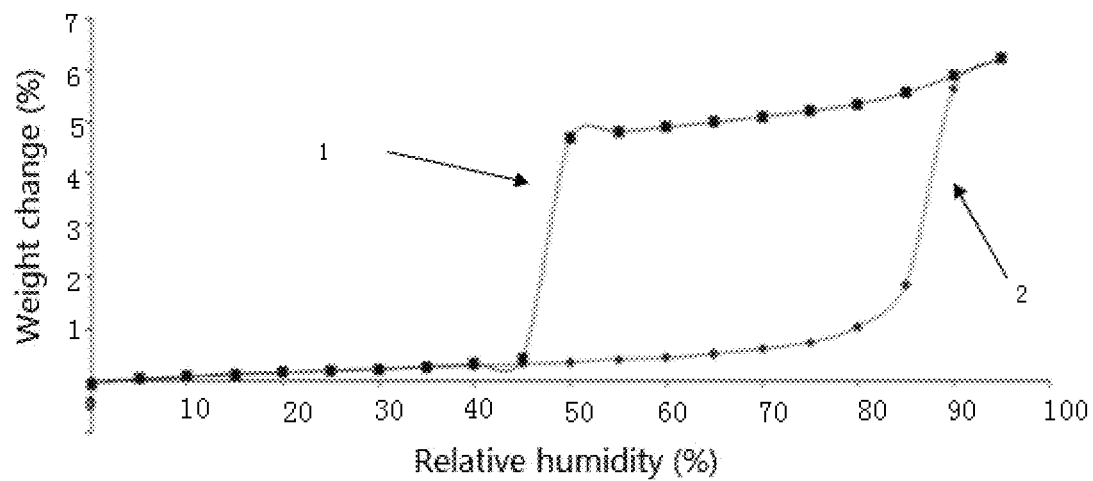
FIG. 9 is the dynamic vapor sorption graph of the crystal form II of the morpholino quinazoline compound represented by formula A obtained by Comparative Example 1; where 1 is the moisture desorption curve and 2 is the moisture absorption curve.

The DVS graph is shown in FIG. 9. The dynamic vapor adsorption graph of the crystal type II of the morpholino quinazoline compound represented by formula A shows a weight gain of 6.237% in the relative humidity from 0% to 95%.

Effect Example 1: Stability

1 Stability of the Crystal Form I of the Morpholino Quinazoline Compound Represented by Formula A in Water and Organic Solvents 1.1 Stability of the Crystal Form I of the Morpholino Quinazoline Compound Represented by Formula a in Water and Organic Solvents at Room Temperature for 10 Days About 20 mg of solid samples of the crystal form I of the morpholino quinazoline compound represented by formula A were weighed respectively and placed into vials, 1 mL of water or organic solvent was added to the vials respectively, and sonicated for 5 min to obtain suspensions. The suspensions were spun at room temperature for 10 days and the filtered wet samples were characterized by XRPD. The results showed that the crystal form did not change in various solvents and remained as crystal form I. The studied solvents included water, methanol, ethanol, ethyl acetate, acetone, methyl tert-butyl ether, acetonitrile, n-hexane, isopropanol, n-heptane, toluene, methyl ethyl ketone, isopropyl ether, isopropyl acetate, n-butanol, aqueous solutions of methanol (90%, 75%, 50%, 10%), aqueous solutions of acetone (95%, 85%, 15%).

1.2 Stability of the Crystal Form I of the Morpholino Quinazoline Compound Represented by Formula A in Organic Solvents with Slurrying at High Temperature for 18 Hours To 5 g of the crystal form I of the morpholino quinazoline compound represented by formula A was added 10 g of ethanol, 10 g of isopropanol, and 10 g of n-heptane. The mixture was slurried at 80° C. for 18 hours, cooled to room temperature, filtered, and dried under vacuum at less than 85° C. for 16 hours to obtain about 4 g of sample. The X-ray powder diffraction pattern of the sample obtained by this method was consistent with the diffraction peaks of the crystal type I sample obtained in Example 1.

The crystal form I of the morpholino quinazoline compound represented by formula A does not change after a long period of time in water and organic solvents at room temperature, as well as at high temperature, which shows that it has good stability in water and organic solvents.

2. Stability of the Crystal Form I of the Morpholino Quinazoline Compound Represented by Formula A Under High Temperature, High Humidity, Illumination Appropriate amount of the samples of the crystal form I of the morpholino quinazoline compound represented by formula A were placed on culture dishes which were then left open under high temperature (40±2° C. and 60±2° C.), high humidity (25° C., RH75±5% and RH90±5%) and illumination (4500±500 Lux, 25° C.) conditions, respectively. Sampling tests were conducted after 5 days, 10 days and one month, and the results are shown in the following Tables 6 to 8.

Appropriate amount of the samples of the amorphous form of the morpholino quinazoline compound represented by formula A and the samples of the crystal form II of the morpholino quinazoline compound represented by formula A were placed on culture dishes respectively, which were then left open under high temperature (60±2° C.), high humidity (25° C., RH75±5%) and illumination (4500±500 Lux, 25° C.) conditions, respectively. Sampling tests were conducted after 5 days, 10 days, and the results are shown in Tables 9 to 10 below.

TABLE 6

Test results under the influencing factor of high temperature (40 ± 2° C., 60 ± 2° C.)

| | Crystal form I of the morpholino quinazoline compound represented by formula A | | | | | | |
|---|---|---|---|---|---|---|---|
| | 40 ± 2° C. | | | 60 ± 2° C. | | | |
| Inspection items | 0 day | 5 days | 10 days | 1 month | 5 days | 10 days | 1 month |
| Total impurities (%) | 0.1% | 0.1% | 0.1% | 0.1% | 0.1% | 0.1% | 0.1% |
| Moisture (%) | 0.07% | 0.1% | 0.2% | 0.1% | 0.2% | 0.2% | 0.1% |
| Crystal form | Crystal form I | Crystal form I | Crystal form I | Crystal form I | Crystal form I | Crystal form I | Crystal form I |

TABLE 7

Test results under the influencing factor of high humidity (25° C., RH 75 ± 5%, RH 90 ± 5%)

| | Crystal form I of the morpholino quinazoline compound represented by formula A | | | | | | |
|---|---|---|---|---|---|---|---|
| | RH 75 ± 5% | | | RH 90 ± 5% | | | |
| Inspection items | 0 day | 5 days | 10 days | 1 month | 5 days | 10 days | 1 month |
| Total impurities (%) | 0.1% | 0.1% | 0.1% | 0.1% | 0.1% | 0.1% | 0.1% |
| Moisture (%) | 0.07% | 0.1% | 0.2% | 0.1% | 0.2% | 0.2% | 0.1% |
| Crystal form | Crystal form I | Crystal form I | Crystal form I | Crystal form I | Crystal form I | Crystal form I | Crystal form I |

TABLE 8

Test results under the influencing factor of illumination (4500 Lux ± 500 Lux, 25° C.

| | Crystal form I of the morpholino quinazoline compound represented by formula A | | | |
|---|---|---|---|---|
| Inspection items | 0 days | 5 days | 10 days | 1 month |
| Total impurities (%) | 0.1% | 0.1% | 0.1% | 0.2% |
| Moisture (%) | 0.07% | 0.1% | 0.1% | 0.1% |
| Crystal form | Crystal form I | Crystal form I | Crystal form I | Crystal form I |

TABLE 9

Test results under the influencing factors of high temperature (60 ± 2° C.), illumination (4500 Lux ± 500 Lux, 25° C.), high humidity (25° C., RH 75 ± 5%)

| Inspection items | | Amorphous form of the morpholino quinazoline compound represented by formula A | | | | | |
|---|---|---|---|---|---|---|---|
| | | 5 days | | | 10 days | | |
| | 0 day | 60° C. | Illumination | 75% RH | 60° C. | Illumination | 75% RH |
| Content (%) | 98.60 | 98.43 | 98.29 | 98.51 | 98.48 | 97.80 | 98.62 |
| Total impurities (%) | 1.32 | 1.54 | 1.68 | 1.37 | 1.46 | 2.16 | 1.31 |

TABLE 10

Test results under the influencing factors of high temperature (60 ± 2° C.), illumination (4500 Lux ± 500 Lux, 25° C.), high humidity (25° C., RH 75 ± 5%)

| Inspection items | | Crystal form II of the morpholino quinazoline compound represented by formula A | | | | | |
|---|---|---|---|---|---|---|---|
| | | 5 days | | | 10 days | | |
| | 0 day | 60° C. | Illumination | 75% RH | 60° C. | Illumination | 75% RH |
| Content (%) | 96.65 | 95.85 | 96.26 | 96.75 | 97.0 | 95.80 | 96.24 |
| Total impurities (%) | 3.28 | 4.04 | 3.64 | 3.18 | 2.97 | 4.14 | 3.61 |

The data of Tables 6 to 8 above show that the crystal form I of the morpholino quinazoline compound represented by formula A has good stability under high temperature, high humidity and illumination conditions without change in chemical purity and crystal form.

After the amorphous samples of the morpholino quinazoline compound represented by formula A were placed under illumination (4500±500 Lux, 25° C.), high temperature (60° C.) and high humidity (25° C., RH75%) conditions for 10 days, respectively, there was no significant changes in the appearance. From the data in Table 9 above, it is clear from the above table that the total impurities content of the samples increases slightly under high temperature (60° C.) and high humidity (25° C., RH75%) conditions; the total impurities content increases significantly under illumination (4500±500 Lux, 25° C.) conditions, indicating the samples are unstable under illumination conditions.

It is more difficult to obtain the crystal form II of the morpholino quinazoline compound represented by formula A, and the purity is also slightly worse. After the samples were placed under illumination (4500±500 Lux, 25° C.), high temperature (60° C.) and high humidity (25° C., RH75%) conditions for 10 days, respectively, there was no significant changes in the appearance. The data in Table 10 above shows that the total impurities content of the samples increases slightly under high temperature (60° C.) and high humidity (25° C., RH75%) conditions; the total impurities content increases significantly under illumination (4500±500 Lux, 25° C.) conditions, indicating the samples are unstable under illumination conditions.

It can be seen that the crystal form I of the morpholino quinazoline compound represented by formula A has good stability under high temperature, high humidity and illumination conditions.

Effect Example 2: Vapor Absorption

About 10 mg of the sample was taken and dried for 60 minutes under a temperature set at 25° C. and a humidity of 0% RH, and then the moisture sorption characteristics of the sample when the humidity changed from 0% RH to 95% RH was tested, and the moisture desorption characteristics of the sample when the humidity changed from 95% RH to 0% RH was tested; the humidity change step was 5% RH; the value of the mass change rate dm/dt less than 0.002% was considered as balance equilibrium, the rate of mass change within 5 minutes less than 0.01%/minute was considered as the equilibrium standard in the testing process, and the maximum equilibrium time was 2 hours. The isothermal water adsorption/desorption characteristics under this test condition were determined and XRPD detection was performed on the samples after the DVS test.

As can be seen from the DVS of the crystal form I of the morpholino quinazoline compound represented by formula A shown in FIG. 5, the crystal form I increases by 0.23% by mass in the relative humidity from 0 to 90% and 0.34% by mass in the relative humidity from 0% to 95% compared to the initial mass.

As can be seen from the DVS of the crystal form II of the morpholino quinazoline compound represented by formula A shown in FIG. 9, the crystal form II of the morpholino quinazoline compound represented by formula A increases by 6.237% by mass in the relative humidity from 0 to 95% compared to the initial mass.

In the relative humidity from 0 to 95%, the weight gain of the crystal form II of the morpholino quinazoline compound represented by formula A is 18 times that of the crystal form I of the morpholino quinazoline compound represented by formula A, which shows that the crystal form I of the morpholino quinazoline compound represented by formula A has less hygroscopicity.

It can be seen that the crystal form I of the morpholino quinazoline compound represented by formula A has good stability and very low hygroscopicity.

It should be understood that the embodiments described herein are for illustrative purposes only, and that adoption of the embodiments will assist in further understanding the present invention, but are not intended to limit the content of the present invention. For those skilled in the art, many changes to both the materials and methods can be implemented without departing from the scope of the present invention, and such changes or improvements are included within the gist and scope of the present application and the scope of the appended claims.

What is claimed is:

1. A crystal form I of the morpholino quinazoline compound represented by formula A having an X-ray powder diffraction pattern comprising diffraction peaks at angles 2θ of 7.7±0.2°, 9.7±0.2°, 12.4±0.2°, 15.4±0.2°, 17.4±0.2°, 18.0±0.2° and 18.4±0.2°,

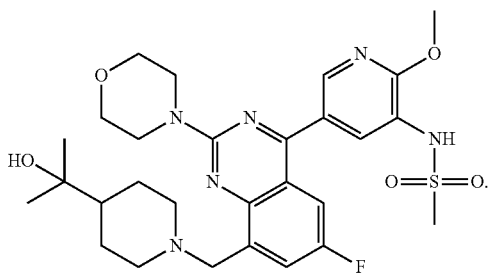

A

2. The crystal form I of the morpholino quinazoline compound represented by formula A of claim 1, wherein the X-ray powder diffraction pattern further comprises diffraction peaks at one or more of the following angles 2θ: 11.0±0.2°, 11.3±0.2°, 19.5±0.2°, 20.1±0.2°, 21.8±0.2°, 22.6±0.2°, 23.2±0.2°, 23.6±0.2°, 24.3±0.2°, 25.8±0.2°, and 28.7±0.2°.

3. The crystal form I of the morpholino quinazoline compound represented by formula A of claim 1, wherein the X-ray powder diffraction pattern comprises diffraction peaks at angles 2θ of 7.7±0.2°, 9.7±0.2°, 11.0±0.2°, 12.4±0.2°, 15.4±0.2°, 17.4±0.2°, 18.0±0.2°, 18.4±0.2°, 23.6±0.2° and 24.3±0.2°;

and/or, the crystal form I of the morpholino quinazoline compound represented by formula A has an infrared absorption spectrum comprising characteristic peaks at 3445 cm$^{-1}$, 3246 cm$^{-1}$, 3018 cm$^{-1}$, 3001 cm$^{-1}$, 2972 cm$^{-1}$, 2953 cm$^{-1}$, 2924 cm$^{-1}$, 2910 cm$^{-1}$, 2891 cm$^{-1}$, 2850 cm$^{-1}$, 1604 cm$^{-1}$, 1589 cm$^{-1}$, 1552 cm$^{-1}$, 1506 cm$^{-1}$, 1489 cm$^{-1}$, 1458 cm$^{-1}$, 1413 cm$^{-1}$, 1365 cm$^{-1}$, 1155 cm$^{-1}$ and 775 cm$^{-1}$;

and/or, the crystal form I of the morpholino quinazoline compound represented by formula A has a differential scanning calorimetry graph having an absorption peak at 204.3±3° C. and a heat of fusion of 98.70 J/g;

and/or, the crystal form I of the morpholino quinazoline compound represented by formula A has a dynamic vapor sorption graph that the crystal form I increases by 0.23% by mass in the relative humidity from 0 to 90% and 0.34% by mass in the relative humidity from 0% to 95% compared to the initial mass.

4. The crystal form I of the morpholino quinazoline compound represented by formula A of claim 3, wherein the X-ray powder diffraction pattern comprises diffraction peaks at angles 2θ of 7.7±0.2°, 9.7±0.2°, 11.0±0.2°, 11.3±0.2°, 12.4±0.2°, 15.4±0.2°, 17.4±0.2°, 18.0±0.2°, 18.4±0.2°, 19.5±0.2°, 20.1±0.2°, 21.8±0.2°, 22.6±0.2°, 23.2±0.2°, 23.6±0.2°, 24.3±0.2°, 25.8±0.2° and 28.7±0.2°;

and/or, the crystal form I of the morpholino quinazoline compound represented by formula A has an infrared absorption spectrum comprising characteristic peaks, vibrational modes, groups and absorption peak intensity shown in the following table;

| Absorption peak wave number (cm$^{-1}$) | Vibrational modes | Group | Absorption peak intensity |
|---|---|---|---|
| 3445 | —O—H stretching vibration | —OH | m |
| 3246 | —N—H stretching vibration | —NH | s |
| 3018, 3001, 2972, 2953, 2924, 2910, 2891, 2850 | —C—H stretching vibration | —CH$_3$, —CH$_2$—, —CH— | m |
| 1604, 1589, 1506, 1489 | Aromatic ring skeleton vibration | Aromatic ring | m |
| 1552 | —NH bending vibration | —NH (methanesulfonamide) | s |
| 1458, 1365 | —C—H bending vibration | —CH$_3$, —CH$_2$—, —CH— | s |
| 1413 | —OH bending vibration (tertiary alcohol) | —OH | s |
| 1365 | —SO$_2$— stretching vibration | —SO$_2$— | s |
| 1155 | —SO$_2$— bending vibration | —SO$_2$— | s |
| 775 | Aromatic ring bending vibration; | Aromatic ring | s | and/or, the crystal form I of the morpholino quinazoline compound represented by formula A has a thermogravimetric analysis graph substantially the same as shown in FIG. 3;

and/or, the crystal form I of the morpholino quinazoline compound represented by formula A has a differential scanning calorimetry graph substantially the same as shown in FIG. 4;

and/or, the crystal form I of the morpholino quinazoline compound represented by formula A has a dynamic vapor sorption graph substantially the same as shown in FIG. 5.

5. The crystal form I of the morpholino quinazoline compound represented by formula A of claim 1, wherein the crystal form I of the morpholino quinazoline compound represented by formula A has an X-ray powder diffraction pattern comprising diffraction peaks at the diffraction angles 2θ with peak height percentage shown in the following table:

| Number | 2θ (±0.2°) | Percentage of peak height (%) |
|---|---|---|
| 1 | 7.239 | 5.5 |
| 2 | 7.666 | 18.4 |
| 3 | 9.732 | 34.5 |
| 4 | 10.962 | 25.7 |
| 5 | 11.318 | 5.4 |
| 6 | 12.385 | 89.2 |
| 7 | 15.377 | 65.5 |
| 8 | 17.404 | 100.0 |
| 9 | 17.971 | 99.4 |
| 10 | 18.382 | 89.6 |
| 11 | 19.516 | 11.0 |
| 12 | 20.111 | 24.6 |
| 13 | 21.795 | 36.0 |
| 14 | 22.551 | 15.8 |
| 15 | 23.191 | 16.5 |
| 16 | 23.564 | 53.2 |

-continued

| Number | 2θ (±0.2°) | Percentage of peak height (%) |
|---|---|---|
| 17 | 24.300 | 30.5 |
| 18 | 25.799 | 13.9 |
| 19 | 28.684 | 21.5. |

6. The crystal form I of the morpholino quinazoline compound represented by formula A of claim 5, wherein the crystal form I of the morpholino quinazoline compound represented by formula A has an X-ray powder diffraction pattern substantially expressed by angle 2θ substantially the same as shown in FIG. 1;
and/or, the crystal form I of the morpholino quinazoline compound represented by formula A has an infrared absorption spectrum substantially the same as shown in FIG. 2.

7. A method of preparing the crystal form I of the morpholino quinazoline compound represented by formula A of claim 1, wherein the method is method 1 or method 2:
method 1: forming the morpholino quinazoline compound represented by formula A in a solvent into a hot saturated solution, and then cooling; the solvent is one or more selected from acetonitrile, 2-methyltetrahydrofuran, acetone, ethyl acetate, ethanol and isopropanol;
method 2: mixing the morpholino quinazoline compound represented by formula A in solvent A and solvent B, dissolving and crystallizing;
the solvent A is one or more selected from tetrahydrofuran, 1,4-dioxane, ethanol, ethyl acetate, N,N-dimethylformamide, N,N-dimethylacetamide, and dimethyl sulfoxide; the solvent B is one or more selected from n-heptane, n-hexane, cyclohexane, cyclopentane, n-pentane, petroleum ether, and water.

8. The method of preparing the crystal form I of the morpholino quinazoline compound represented by formula A of claim 7, wherein, in method 1, the cooling is performed by rapid cooling method or slow cooling method; when the cooling is performed by rapid cooling method, then the final temperature of the cooling is −15 to −25° C.; when the cooling is performed by slow cooling method, then the cooling is performed at a rate of 5 to 15° C./h;
and/or, in method 2, when the solvent A is one or more selected from tetrahydrofuran, 1,4-dioxane, ethanol and ethyl acetate, then the solvent B is one or more selected from n-heptane, n-hexane, cyclohexane, cyclopentane, n-pentane and petroleum ether;
and/or, when the solvent A is one or more selected from N,N-dimethylformamide, N,N-dimethylacetamide and dimethyl sulfoxide (DMSO), then the solvent B is water;
and/or, the method 2 comprises dissolving the morpholino quinazoline compound represented by formula A in the solvent A to obtain a mixed solution, adding the solvent B to the mixed solution and crystallizing.

9. A pharmaceutical composition comprising the crystal form I of the morpholino quinazoline compound represented by formula A of claim 1, and a pharmaceutically acceptable carrier.

10. A method of treating a disease associated with PI3 kinase, comprising administering to a subject in need of the treatment a therapeutically effective amount of the crystal form I of the morpholino quinazoline compound represented by formula A of claim 1, wherein the disease associated with PI3 kinase is selected from the group consisting of rheumatoid arthritis, psoriasis, ulcerative colitis, Crohn's disease, and systemic lupus erythematosus, hematologic neoplasms, asthma and atopic dermatitis.

* * * * *